United States Patent
Tarassenko et al.

(10) Patent No.: US 10,448,846 B2
(45) Date of Patent: Oct. 22, 2019

(54) METHOD AND APPARATUS FOR MEASURING AND DISPLAYING A HAEMODYNAMIC PARAMETER

(71) Applicant: OXFORD UNIVERSITY INNOVATION LIMITED, Botley, Oxford (GB)

(72) Inventors: Lionel Tarassenko, Oxford (GB); Jonathan Daly, Oxford (GB)

(73) Assignee: OXFORD UNIVERSITY INNOVATION LIMITED, Botley, Oxford (GB)

( * ) Notice: Subject to any disclaimer, the term of this patent is extended or adjusted under 35 U.S.C. 154(b) by 302 days.

(21) Appl. No.: 15/536,588

(22) PCT Filed: Dec. 14, 2015

(86) PCT No.: PCT/GB2015/053973
§ 371 (c)(1),
(2) Date: Jun. 15, 2017

(87) PCT Pub. No.: WO2016/097708
PCT Pub. Date: Jun. 23, 2016

(65) Prior Publication Data
US 2017/0354334 A1 Dec. 14, 2017

(30) Foreign Application Priority Data
Dec. 16, 2014 (GB) .................. 1422369.7

(51) Int. Cl.
*A61B 5/02* (2006.01)
*A61B 5/024* (2006.01)
(Continued)

(52) U.S. Cl.
CPC ........ *A61B 5/02427* (2013.01); *A61B 5/0077* (2013.01); *A61B 5/0261* (2013.01);
(Continued)

(58) Field of Classification Search
USPC ...................................... 382/128
See application file for complete search history.

(56) References Cited

U.S. PATENT DOCUMENTS 6,331,162 B1    12/2001   Mitchell
6,549,801 B1 *   4/2003   Chen ............... A61B 5/0073
                                              250/350
(Continued)

FOREIGN PATENT DOCUMENTS

WO   WO-2004/052195 A1   6/2004
WO   WO-2010/100593 A1   9/2010
(Continued)

OTHER PUBLICATIONS

Kamshilin, Alexei A. et al: "Variability of Microcirculation Detected by Blood Pulsation Imaging", PLOS ONE, vol. 8, No. 2, Feb. 19, 2013 (Feb. 19, 2013), pp. 1-9, XP055114101, DOI: 10.1371/journal.pone.0057117.
(Continued)

*Primary Examiner* — Ishrat I Sherali
(74) *Attorney, Agent, or Firm* — Harness, Dickey & Pierce, P.L.C.

(57) ABSTRACT

Haemodynamic parameters such as the amplitude and phase of a pulse wave passing through a region of interest can be obtained from a video image of the exposed skin of a patient by processing of the reflectance photoplethysmographic signal using signal averaging. The region of interest is defined and a reflectance photoplethysmographic signal obtained by finding the mean pixel intensity across the region of interest for each video frame. Signal averaging is performed on the resulting pulsatile waveform by detecting peaks in the waveform, selecting those parts of the waveform which lie within a window centered on the peaks, and summing the selected parts of the waveform to find an average pulse waveform. The region of interest is then
(Continued)

divided into sub-regions and an average pulse waveform for the video sequence is found for each of the sub-regions in the same way. The amplitudes of the average pulse waveforms for the sub-regions can be measured and displayed, for example as a spatial map across the region of interest. The phase of the average pulse waveforms in the sub-regions in the sub-regions relative to the average pulse waveform for the whole region of interest can be measured and displayed, again as a spatial map. The phase and amplitude maps give an indication of the quality of perfusion across the region of interest.

13 Claims, 6 Drawing Sheets

(51) Int. Cl.
    *A61B 5/00*            (2006.01)
    *A61B 5/026*         (2006.01)

(52) U.S. Cl.
    CPC .............. *A61B 5/725* (2013.01); *A61B 5/742* (2013.01); *A61B 5/748* (2013.01); *A61B 2576/02* (2013.01)

(56) References Cited

U.S. PATENT DOCUMENTS

| | | | | |
|---|---|---|---|---|
| 8,542,878 | B2* | 9/2013 | Cennini | G06K 9/00255 |
| | | | | 382/103 |
| 8,768,438 | B2* | 7/2014 | Mestha | A61B 5/0044 |
| | | | | 600/473 |
| 2015/0313502 | A1* | 11/2015 | Mestha | A61B 5/0295 |
| | | | | 600/473 |
| 2016/0317018 | A1* | 11/2016 | Sakagawa | A61B 3/102 |
| 2017/0347967 | A1* | 12/2017 | Guazzi | A61B 5/6898 |
| 2018/0153455 | A1* | 6/2018 | Guazzi | A61B 5/0077 |
| 2018/0279874 | A1* | 10/2018 | Yoshida | A61B 3/10 |

FOREIGN PATENT DOCUMENTS

| | | |
|---|---|---|
| WO | WO-2013/027027 A2 | 2/2013 |
| WO | WO-2015/055405 A1 | 4/2015 |
| WO | WO 2016097708 * 12/2015 | ............... A61B 5/00 |

OTHER PUBLICATIONS

Zaproudina, Nina et al: "Asynchronicity of Facial Blood Perfusion in Migraine", PLOS ONE, vol. 8, No. 12, Dec. 4, 2013 (Dec. 4, 2013), pp. 1-9, XP055253614, DOI: 10.1371/journal.pone. 0080189.

Zheng, Jia et al: "A remote approach to measure blood perfusion from the human face", Proceedings of SPIE, vol. 7169, Jan. 1, 2009 (Jan. 1, 2009), pp. 716917-1-716917-7, XP055018740, ISSN: 0277-786X, DOI: 10.1117/12.807354.

Verkruysse, Wim et al: "Remote plethysmographic imaging using ambient light", Optics Express, vol. 16, No. 26, Dec. 22, 2008 (Dec. 22, 2008), pp. 21434-21445, XP055065281, ISSN: 1094-4087, DOI: 10.1364/OE.16.021434.

International Search Report and Written Opinion of the International Searching Authority issued in PCT/GB2015/053973, dated Mar. 9, 2016, ISA/EPO.

GB Search Report of the Intellectual Property Office under Section 17 issued in application No. GB1422369.7, dated Jun. 16, 2015.

* cited by examiner

METHOD AND APPARATUS FOR MEASURING AND DISPLAYING A HAEMODYNAMIC PARAMETER

CROSS REFERENCE TO RELATED APPLICATIONS

This application is a U.S. National Phase Application under 35 U.S.C. 371 of International Application No. PCT/GB2015/053973 filed on Dec. 14, 2015 and published in English as WO 2016/097708 A1 on Jun. 23, 2016. This application is based on and claims the benefit of priority from Great Britain Patent Application No. 1422369.7 filed Dec. 16, 2014. The entire disclosures of all of the above applications are incorporated herein by reference.

The present invention relates to the measuring and displaying of a haemodynamic parameter, for example parameters relating to the perfusion level, and direction and timing of blood flow. In more detail it relates to obtaining such parameters by processing a video recording of the skin of a human subject.

Camera-based measurement of the vital signs of a human subject is a known technique for contactless medical monitoring of patients. Contactless monitoring is particularly useful because it avoids the problems with contact-based sensors where movement of the patient disturbs the sensor or causes it to become detached. In a typical camera-based arrangement a video camera is positioned so that the bare skin of the subject, i.e. the patient to be monitored, is within the field of view of the video camera. WO-A2-2013/027027, for example, discloses deriving measures of the heart rate and breathing rate from a photoplethysmographic image (PPGi) formed by the remote reflectance photoplethysmography (rPPG) signal. The rPPG signal is a variation in reflectance of light at certain wavelengths as the volume of blood in the skin capillaries varies with the cardiac cycle. Although invisible to normal sight, the skin can effectively be regarded as pulsing more red and less red with each heart beat. This change can be detected in a standard colour video image of the skin taken with a normal video camera such as a webcam. The region of interest from which the rPPG signal is obtained can be selected manually or automatically using well-known video image analysis techniques, or once selected manually, the region of interest can then be tracked as the patient moves.

While previous rPPG analysis has concentrated on finding heart rate and breathing rate, the present inventors have realised that there are other parameters of interest which are relevant to a patient's health and which can be derived from the rPPG signal. For example, particularly in the case of neonates there is interest in the degree of perfusion in the skin (i.e. the amount of blood flow through different skin regions) because a decline in perfusion can be indicative of septic shock. Further, it is frequently required to take blood from a patient and locating well-perfused areas from which to extract blood is advantageous, again particularly in the case of neonates. It is also known that changes in the pulse transit time (i.e. the time taken for a pulse to travel between two sites within the body) is correlated to blood pressure so that increases in pulse transit time can indicate decreases in blood pressure (and vice-versa). Being able to detect haemodynamic parameters like these in a contactless manner would be advantageous.

Accordingly, the present invention provides a method of measuring and displaying a haemodynamic parameter comprising the steps of: acquiring a video image of a region of interest on the skin of a subject; processing the video image to obtain a first remote reflectance photoplethysmogram signal for the region of interest; performing signal averaging on the first remote reflectance photoplethysmogram signal for the region of interest to obtain a reference average pulse waveform; splitting the region of interest into plural subsidiary regions of interest and processing the video signal to obtain a subsidiary remote reflectance photoplethysmogram signal for each subsidiary region of interest, performing signal averaging on each subsidiary remote reflectance photoplethysmogram signal to obtain a subsidiary average pulse waveform for each subsidiary region of interest; determining the phase difference between each subsidiary average pulse waveform and the reference average pulse waveform; and displaying as said haemodynamic parameter the phase difference for each subsidiary region of interest.

The present invention utilises the technique of signal averaging in a region of interest, and then in sub-areas of the region of interest, to determine how a pulse wave moves through the region of interest. For example, if a pulse wave moves from left to right through a region of interest, sub-areas of the region of interest will show a subsidiary pulse wave which is advanced compared to the overall average pulse wave while sub-areas to the right of the region will show a phase of subsidiary pulse wave which is retarded with respect to (later than) the overall average pulse wave. As the pulse wave moves across the region more quickly, the phase differences will decrease, whereas if the pulse wave moves more slowly, the phase differences will increase. Further, varying phase differences from sub-area to sub-area show different timings of the arrival of the pulse wave in those areas, giving an indication of local perfusion.

The technique of signal averaging is based on increasing the strength of a signal relative to uncorrelated noise by averaging a set of replicate measurements. The assumption is that while the signal is constant and correlated in the replicate measurements, the noise is random (with zero mean and constant variance), so that summing the measurements strengthens the signal preferentially compared to the noise. With the present invention the signal averaging concept is applied by averaging successive pulse waves in an rPPG signal to obtain an average pulse wave over a certain period. The period may be from 10 seconds (for patients such as neonates with fast heart rates) up to two minutes, more preferably up to one minute. For an adult with a typical heart rate of 72 beats per minute (BPM), this would therefore result in averaging 72 pulse waves.

Preferably the signal averaging performed on each subsidiary rPPG signal (i.e. within each subsidiary region of interest) is performed by averaging sections of the rPPG signal (windows) selected with reference to reference time points which are the same as the reference time points used for signal averaging over the whole region of interest. The reference time points may be the time of occurrence of peaks in the rPPG signal for the whole region of interest. The reference time points may however be other repeating recognisable signal features such as minima. The reference time points may be obtained from salient points in other physiological signals such as the electrocardiogram (ECG), but in the preferred embodiment of the invention there is no other sensor used other than the video camera.

The windows may be centered on the reference time points, or may be otherwise positioned e.g. may start or finish on the reference time points. The size of the window is preferably set in dependence upon the expected pulse rate of the subject. For example for neonates, with a high pulse rate, the windows may be 0.4 seconds long, but for adults, with slower pulse rates, the windows may be one second long. The window preferably extends approximately between the minima (troughs) either side of a maximum (peak) representing a pulse, thereby encompassing an entire cardiac cycle. The window size may be varied automatically in dependence upon the detected heart rate or the timing of the reference time points, or may be set to extend between certain recognisable signal features—e.g. from one minimum or maximum to the next.

The rPPG signal is preferably obtained by averaging the pixel intensities of a colour channel of the video image over the region of interest or subsidiary region of interest. All three colour channels in a conventional video signal may be separately averaged to produce three measurements of the haemodynamic parameter or only one colour channel may be used, or results from the three colour channels may be combined or selected amongst depending on the quality of the signal.

Preferably the rPPG signal is band-pass filtered to concentrate on the frequencies of interest (i.e. the expected pulse rates), for example by using a band-pass filter with cut-off frequencies at 0.5 Hz and 5 Hz (corresponding to pulse rates of 30 and 300 BPM), or narrower. For example, for neonatal patients the filter may have cut-off frequencies of 1.5 Hz (90 BPM) and 5 Hz (300 BPM) and for adult patients the filter may have cut-off frequencies of 0.6 Hz (36 BPM) and 2.2 Hz (132 BPM). Preferably the band-pass filtered rPPG signal is re-sampled to produce smoother waveforms and hence improve identification of maxima and minima in the waveform, before signal averaging is performed.

Although the main parameter of interest is the phase difference between the average pulse waveforms in each subsidiary region of interest, the amplitude of the average pulse waveform in each subsidiary region of interest may be measured and displayed. The amplitude gives a direct indication of the level of perfusion of the subsidiary region of interest, though it can be affected by confounding factors such as the brightness of illumination and the angle of the reflecting skin region with respect to the ambient illumination The phase differences and amplitudes may be displayed as maps, for example by intensity-coding or colour-coding the different phase differences and amplitudes and displaying them on a representation of the region of interest. Such a map can be superimposed on the original video image of the patient.

The subsidiary regions of interest may be formed as a simple grid within the overall region of interest, and each subsidiary region of interest may cover about ten pixels of the video signal, for example from 5 to 50 pixels, more preferably from 10 to 20 pixels, though the resolution can be increased or decreased according to the application. Alternatively, instead of a rectangular grid of subsidiary regions of interest, the region of interest can be divided in other ways.

The invention may be embodied in a computer program comprising program code for causing a programmed computer to execute the method on an acquired video signal. Furthermore, the invention extends to an apparatus comprising a video camera for acquiring a video image of a region of interest on the skin of a subject, an image processor, such as a computer, for executing the method on the acquired image, and a display for displaying the haemodynamic parameter or parameters.

The invention will be further described by way of example with reference to the accompanying drawings in which:—

An embodiment of the invention will now be described which consists of three main steps: the derivation of the remote reflectance photoplethysmography (rPPG) signal from video, the processing of the rPPG signal using signal averaging, and spatial mapping of the derived haemodynamic parameters.

Figure 1A:
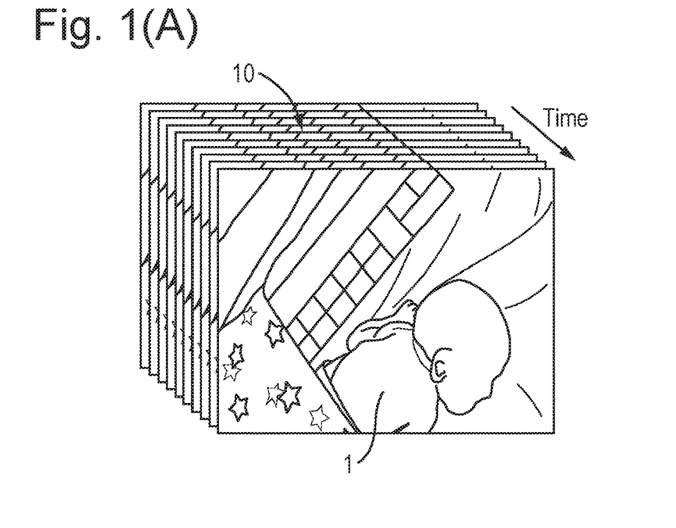
FIG. 1A schematically illustrates a series of image frames of a subject forming a video image.
Figure 1B:
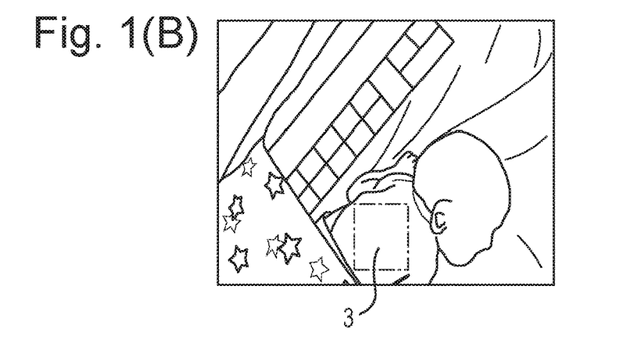
FIG. 1B illustrates a region of interest on the skin of a subject.
Figure 1C:
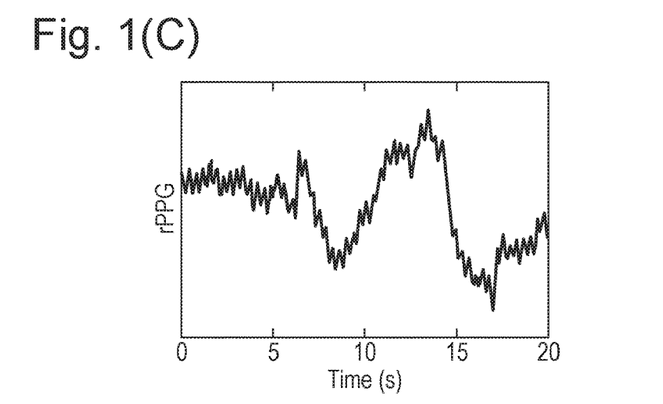
FIG. 1C illustrates a raw rPPG signal obtained from the region of interest illustrated in FIG. 1B.
Figure 6:
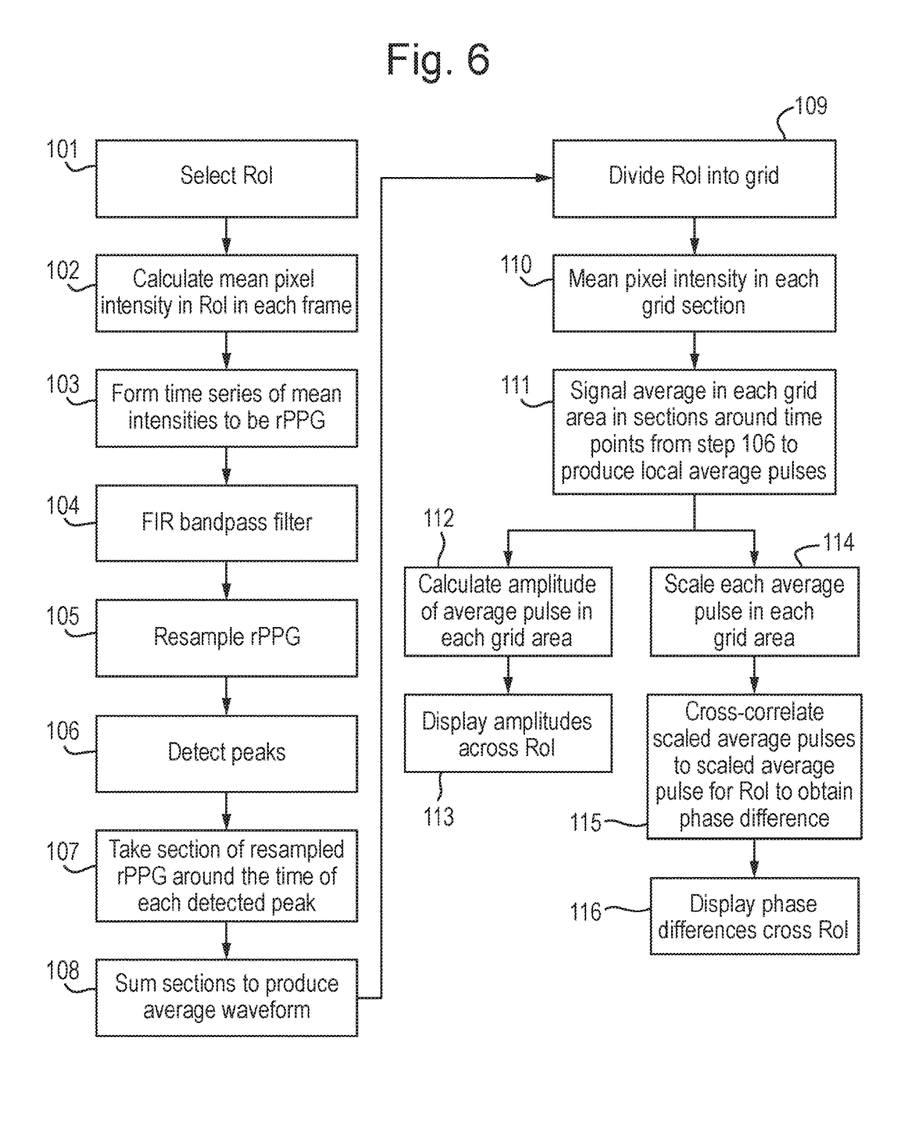
FIG. 6 is a flow diagram explaining the processing in accordance with one embodiment of the invention.

As explained above the rPPG signal measures colour changes in the skin caused by changes in blood volume in the skin capillaries. The rPPG signal can be obtained by measuring the amount of ambient light reflected from a subject's skin using a video camera placed up to two meters away. FIG. 1 schematically illustrates the process and FIG. 7 the apparatus. FIG. 1A represents a video signal as a plurality of image frames 10 of a subject 1, in this case a neonatal patient. As illustrated in FIG. 1B a region of interest 3 on the skin of the patient 1 is defined. The region of interest 3 may be manually defined, as indicated in step 101 of FIG. 6, and maintained in the same place from frame to frame, or it may track movement of the patient 1 using conventional motion tracking techniques. Alternatively the region of interest 3 may be automatically selected by recognising skin areas in the image using known image recognition techniques. For each frame 10 of the video sequence the mean pixel intensity in the region of interest 3 is calculated, as indicated in step 102. Each of the three RGB colour channels is treated separately. These mean pixel intensities are then formed into a time-series, as indicated in step 103, which represents the rPPG signal for the region of interest, as illustrated in FIG. 1C (for one colour channel).

Figure 2A:
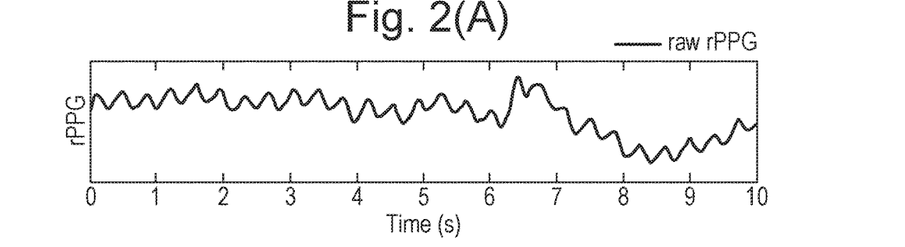
FIG. 2A illustrates a raw rPPG signal.

FIG. 2A illustrates 10 seconds of a raw rPPG signal and the periodic pulse waveform can easily be seen. This periodicity can be exploited by using a technique based on signal averaging to increase the signal-to-noise ratio and thus reduce effects such as low-frequency artefacts caused by subject movement or changes in ambient lighting, as well as higher frequency noise due to the flickering of artificial lighting and electronic noise on the camera's image sensor. In general terms signal averaging involves adding each of the individual pulse waveforms in the rPPG signal over a certain time period to produce an average pulse waveform for that period. In more detail, in step 104 the raw rPPG signal is filtered using a finite impulse response (FIR) band-pass filter, e.g. with the filter response illustrated in FIG. 2D. In this embodiment an FIR filter with an order 100 was selected and the cut-off frequencies are chosen according to the expected pulse rate of the patient. For neonatal patients the filter can have cut-off frequencies of 1.5 Hz and 5 Hz (corresponding to heart rates of 90 to 300 BPM) whereas for adult patients the filter can have cut-off frequencies of 0.6 Hz and 2.2 Hz corresponding to heart rates of 36 to 132 BPM. Rather than pre-setting the cut-off frequencies, these may be varied based on a detected pulse rate.

Figure 2B:
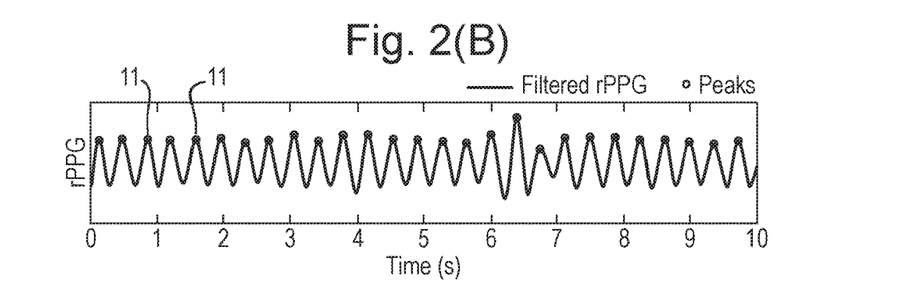
FIG. 2B illustrates peak detection in a band-pass filtered version of the rPPG signal of FIG. 2A.

Then in step 105 the raw rPPG signal is resampled, in this case to 1 kHz using cubic spline interpolation and then in step 106 peak detection is performed on the resampled signal, in this embodiment using a decaying threshold to allow for sudden changes in amplitude. FIG. 2B illustrates the resampled signal with detected peaks indicated by circles. Resampling with cubic spline interpolation allows the peak and trough locations to be estimated more accurately (when assumptions about the rPPG signal are taken into account, namely that it is smooth and approximately sinusoidal).

Figure 2C:
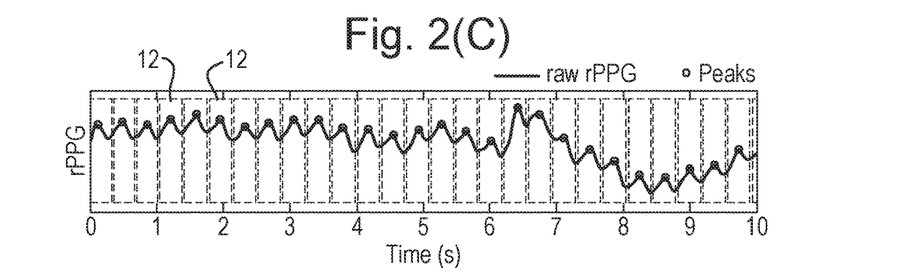
FIG. 2C illustrates the setting of windows around each peak in the filtered rPPG signal.
Figure 2D:
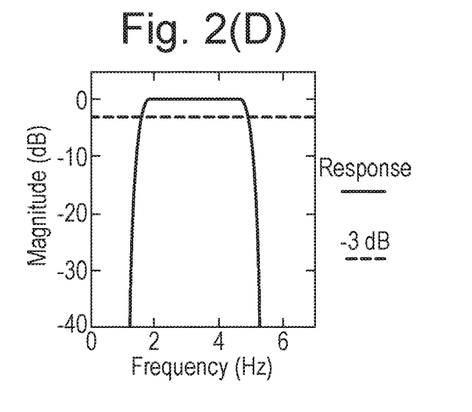
FIG. 2D illustrates the response of the band-pass filter used in the embodiment of FIG. 2.

Then in step 107, for each peak found in step 105 the location of the peak is taken as a reference time point 11 and a section of the re-sampled raw rPPG signal around the reference time point 11 is selected. These sections can be regarded as windows 12 centred on the reference time points 11 as illustrated in FIG. 2C. The length of the window 12 depends on the pulse rate and can be, for example, 0.4 seconds for neonates and 1 second for adults, though different window lengths are possible. Typically, the window length is chosen to be approximately the time taken for one cardiac cycle (e.g. 1 second for a typical pulse rate of 60 BPM). It is also possible to adjust the window length in dependence upon the detected pulse rate.

Figure 2E:
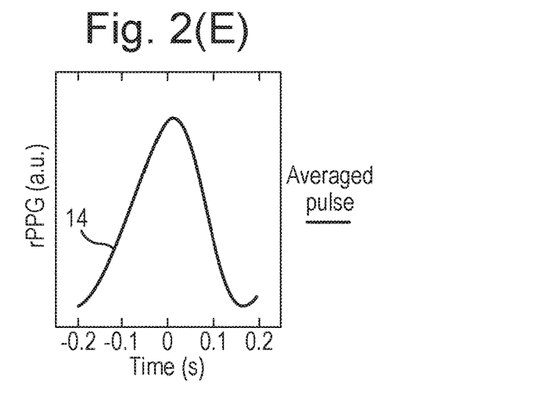
FIG. 2E illustrates an average pulse waveform obtained by signal averaging the rPPG signal of FIG. 2A.

In step 108 the selected sections of the re-sampled rPPG signal for this section of video are summed, sample by sample, after synchronisation with respect to the salient point at the centre of the window (i.e. the peak as in FIG. 2) and scaled to produce a single average waveform as illustrated in FIG. 2E. Thus in the example of FIG. 2, each 10-second section of video would produce three average waveforms, one for each of the three colour channels. The process can then be repeated for the next 10-second section of video. The next section can follow contiguously, or can overlap the previous section, e.g. 10-second windows which are slid by a step of, for example, 1 second each time.

Figure 3A:
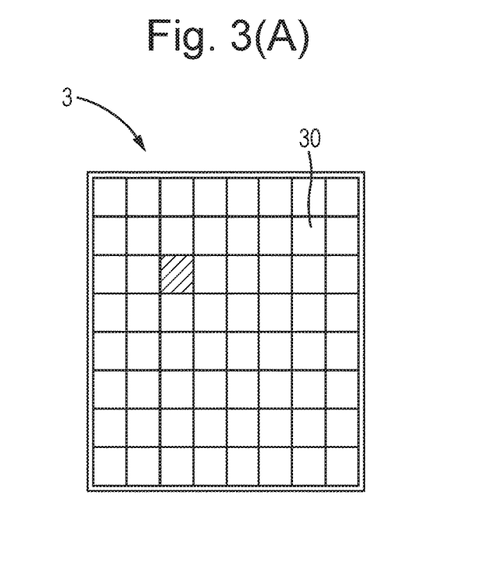
FIG. 3A illustrates the division of the region of interest into subsidiary regions of interest according to one embodiment of the invention.

The average waveform 14 illustrated in FIG. 2E is effectively a reference average pulse waveform for the whole of the region of interest 3. To obtain haemodynamic parameters for the region of interest 3, it is then, in step 109, divided into plural subsidiary regions of interest 30, for example in a rectangular grid as illustrated in FIG. 3A. Signal averaging is then repeated for each of the subsidiary regions of interest 30 again separately on each of the three colour channels. Thus in step 110 the mean pixel intensity in each subsidiary region of interest for each frame in the video sequence is obtained to construct a local rPPG signal for that subsidiary region of interest. In step 111 using the reference time points 11 from the peak detection process of step 106, and using corresponding windows 12 centred on each reference time point, the local rPPG signal within each window 12 are summed and scaled to produce a subsidiary average pulse waveform for that subsidiary region of interest 30. Each subsidiary region of interest 30 will have its own subsidiary average pulse waveform for each colour channel and each (10-second in this example) section of video signal.

Figure 4A:
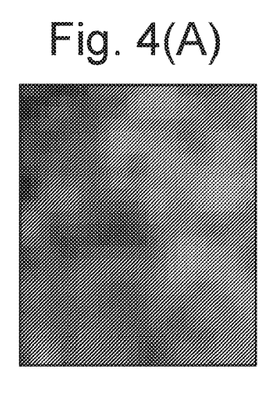
FIGS. 4A-C illustrate maps of local rPPG phase for the three colour channels measured with one embodiment of the invention.
Figure 4B:
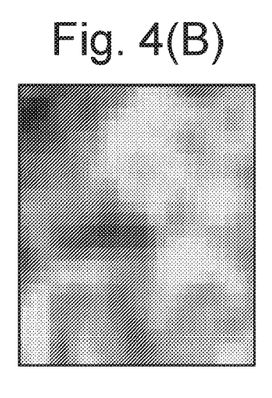
Figure 4C:
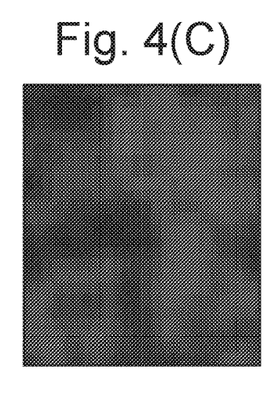
Figure 4D:
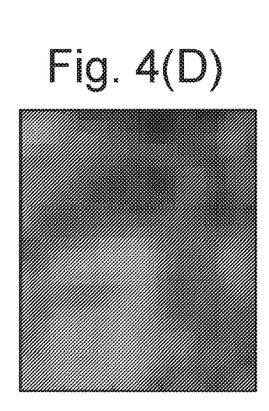
FIGS. 4D-F illustrate the local rPPG amplitude for the 3 colour channels of an rPPG signal.
Figure 4E:
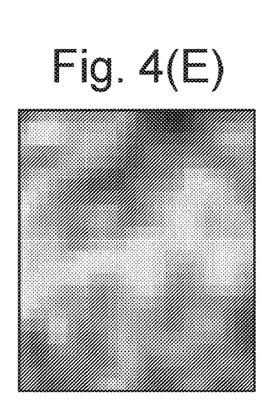
Figure 4F:
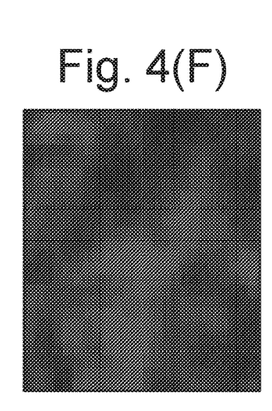

Then the phase and amplitude of the local pulse waveforms 140 for the subsidiary regions of interest 30 can be calculated. The amplitude is calculated in step 112 by subtracting the minimum of the subsidiary average pulse waveform 140 from its maximum and the amplitude for each subsidiary region of interest 30 is intensity coded and displayed in a map for each colour channel as illustrated in FIGS. 4D, E and F.

To find the phase of the subsidiary average pulse waveform 140 in each subsidiary region of interest 30, each subsidiary average waveform 140 and the reference average waveform 14 for the whole region of interest are firstly scaled to take values between 0.0 and 1.0 by subtracting their minimum and dividing by their range. Other ways of normalising the waveforms to have approximately equal (peak–trough) amplitude can be used instead, such as, for each waveform, subtracting its mean value and dividing by its standard deviation.

Figure 3B:
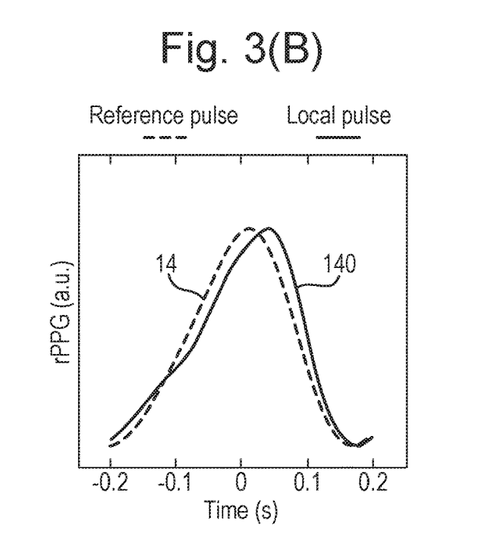
FIG. 3B illustrates the reference average pulse waveform for the whole region of interest and a subsidiary average pulse waveform for one of the subsidiary regions of interest of FIG. 3A.
Figure 3C:
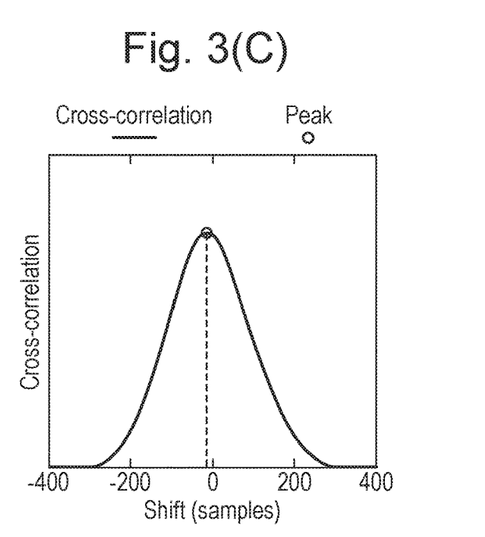
FIG. 3C illustrates the calculation of the phase difference using cross-correlation.

FIG. 3B illustrates one of the scaled subsidiary average pulse waveforms 140 and the scaled reference average waveform 14. Then the cross-correlation of each of the subsidiary average pulse waveforms 140 with the reference average pulse waveform 14 is calculated for a variety of phase shifts and the phase difference is taken to be that phase shift at which the cross-correlation has its maximum value. FIG. 3C illustrates the cross-correlation between the two pulse waveforms of FIG. 3B for a range of phase shifts up to one pulse width either side, from −400 to +400 samples (i.e. from −0.4 s to +0.4 s, given the 1 kHz resampling frequency in this embodiment) in the illustrated example. It can be seen that the cross-correlation has a maximum value at a phase shift of minus 14 samples, which corresponds to a time lag of plus 14 ms. The phase difference in each of the subsidiary regions of interest 30 can be intensity coded and displayed as a map for each of the three RGB colour channels as shown in FIGS. 4A, B and C. Rather than intensity coding, colour coding can be used. To reduce noise in the maps, the maps can be spatially filtered, for example using a three-by-three pixel Gaussian filter. The maps in FIGS. 4A-F are based on averaging pulse waveforms for a one-minute section of video (rather than 10 seconds illustrated in FIGS. 2A to C). However different lengths of video may be averaged.

Figure 5A:
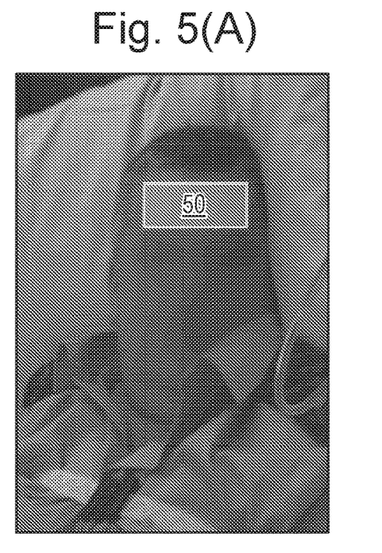
FIG. 5A illustrates a region of interest in an image of an adult patient and FIGS. 5B and 5C illustrate maps of the local rPPG phase and amplitude respectively for the adult patient.
Figure 5B:
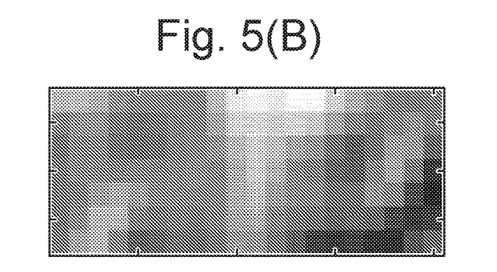
Figure 5C:
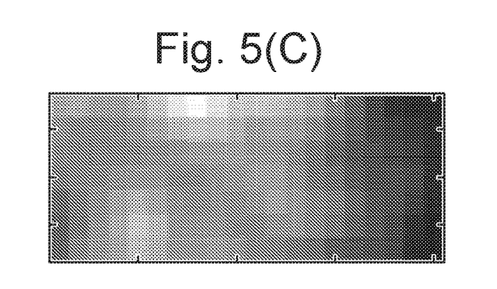
Figure 7:
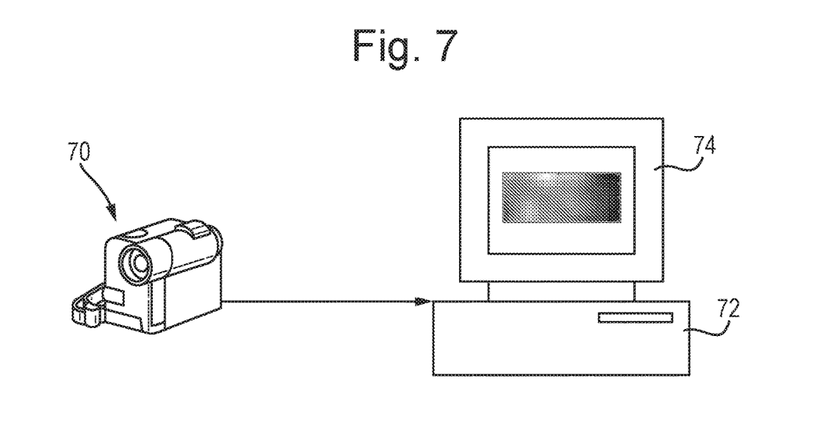
FIG. 7 schematically illustrates an apparatus for executing the method of one embodiment of the invention.

FIG. 5 illustrates a single frame from a video sequence of an adult patient with the region of interest 50 outlined. FIGS. 5B and C show phase and amplitude maps respectively for one minute of video in this case for a monochrome camera with only one channel. Referring to FIG. 5B it can be seen that advanced phase (darker) areas are towards the bottom right of the region of interest and generally retarded phase (lighter areas) towards the top and left hand side. This shows that the pulse wave in this case generally travels from bottom to top. FIG. 7 schematically illustrates the apparatus required for the invention. The video signal may be acquired by a standard monochrome or colour video camera 70 and the output provided to a general purpose computer 72 programmed to execute the signal averaging processes and amplitude and phase difference calculations explained above and illustrated with reference to FIGS. 1 to 6. The amplitude and phase differences may be displayed on a display 74 either as spatial maps as shown in FIGS. 4A-F and FIGS. 5B and C, or as charts or values.

The invention claimed is:

1. A method of measuring and displaying a haemodynamic parameter comprising the steps of:
    acquiring a video image of a region of interest on the skin of a subject;
    processing the video image to obtain a first remote reflectance photoplethysmogram signal for the region of interest;
    performing signal averaging on the first remote reflectance photoplethysmogram signal for the region of interest to obtain a reference average pulse waveform;
    splitting the region of interest into plural subsidiary regions of interest and processing the video signal to obtain a subsidiary remote reflectance photoplethysmogram signal for each subsidiary region of interest, performing signal averaging on each subsidiary remote reflectance photoplethysmogram signal to obtain a subsidiary average pulse waveform for each subsidiary region of interest;
    determining the phase difference between each subsidiary average pulse waveform and the reference average pulse waveform; and
    displaying as said haemodynamic parameter the phase difference for each subsidiary region of interest.

2. The method according to claim 1 wherein the signal averaging is performed on each subsidiary remote reflectance photoplethysmogram signal using reference time points defined for the signal averaging used to obtain the reference average pulse waveform.

3. The method according to claim 2 wherein the reference time points are the times of occurrence of repeated signal features, such as peaks, in the first remote reflectance photoplethysmogram signal.

4. The method according to claim 2 wherein the signal averaging comprises defining respective windows positioned with respect to each the reference time points and summing the signals in the windows.

5. The method according to claim 4 wherein the size of the window is set in dependence upon the expected pulse rate of the subject.

6. The method according to claim 1 wherein the remote reflectance photoplethysmogram signal is resampled before signal averaging is performed.

7. The method according to claim 1 wherein the remote reflectance photoplethysmogram signal is bandpass filtered before signal averaging is performed.

8. The method according to claim 7 wherein the passband for the bandpass filtering is set in dependence upon the expected pulse rate of the subject.

9. The method according to claim 1 wherein the remote reflectance photoplethysmogram signal is obtained by averaging pixel intensities of the video image over the region of interest.

10. The method according to claim 1 further comprising measuring the amplitude of each subsidiary average pulse wave and displaying the amplitude as a second haemodynamic parameter.

11. The method according to claim 1 wherein the haemodynamic parameter or parameters for each subsidiary region are displayed as a map.

12. A non-transitory computer readable medium storing a computer program comprising a program code that causes a programmed computer to execute on an acquired video signal the method of claim 1.

13. An apparatus comprising a video camera for acquiring a video image of a region of interest on the skin of a subject, an image processor for executing on the acquired image the method of claim 1, and a display for displaying the haemodynamic parameter.

* * * * *